United States Patent [19]

Crowley et al.

[11] Patent Number: 5,492,819
[45] Date of Patent: Feb. 20, 1996

[54] RECOVERY OF INSOLUBLE BIOSYNTHETIC PRODUCTS

[75] Inventors: Richard P. Crowley, Westborough, Mass.; Jeffrey M. Gerstner, Bloomfield, N.Y.

[73] Assignee: Genencor International, Inc., Rochester, N.Y.

[21] Appl. No.: 125,997

[22] Filed: Sep. 23, 1993

[51] Int. Cl.⁶ ................................ C12P 17/10
[52] U.S. Cl. .................. 435/121; 435/127; 435/261
[58] Field of Search .................. 435/127, 261, 435/121

[56] References Cited

U.S. PATENT DOCUMENTS

| | | | |
|---|---|---|---|
| 4,520,103 | 5/1985 | Ensley, Jr. | 435/121 |
| 4,752,301 | 6/1988 | Koch | 8/653 |
| 4,992,556 | 2/1991 | Takaki et al. | 548/457 |
| 5,082,936 | 1/1992 | Jamas et al. | 536/123 |
| 5,164,485 | 11/1992 | Yukio et al. | 530/350 |
| 5,175,096 | 12/1992 | Hook et al. | 435/69.1 |

OTHER PUBLICATIONS

Derwent Abs 85–286695/46 of JP60196195 (Oct. 4, 1995) Dainippon Seito KK.

*Primary Examiner*—Herbert J. Lilling
*Attorney, Agent, or Firm*—Margaret A. Horn

[57] ABSTRACT

There is disclosed a process for the recovery of an insoluble fermentation product from a solid phase cell mass, the process comprising treating the fermentation broth to solubilize the cell mass and separating by known methods the liquid phase from the insoluble (product-containing) phase. The solubilization of the cell mass may be carried out by one or mere treatments with an alkali or acid compound or by enzymatic treatment of the cell mass to lyze the cells.

5 Claims, 4 Drawing Sheets

RECOVERY OF INSOLUBLE BIOSYNTHETIC PRODUCTS

FIELD OF THE INVENTION

This invention relates to a novel recovery process for the recovery of a desired insoluble fermentation product from a cell mass-containing fermentation broth, the process comprising solubilizing the solid cell mass phase of the fermentation broth by treating the broth with an appropriate alkali or acid one or more times and subsequently separating the resulting liquid phase from the solid (product-containing) phase.

BACKGROUND OF THE INVENTION

Most fermentation products are soluble in the fermentation medium. Examples of such products are enzymes, amino acids and organic acids. This allows separation of the fermentation product from the cell mass by typical liquid-solid separation technologies (for example, centrifuges, filters or settlers). Fermentation products that are insoluble in an aqueous fermentation broth are often purified by extraction into a solvent in which the product is more soluble than the aqueous fermentation broth, thus, separating the product from the cell mass. Examples are sterols and lipids.

Products exist that are insoluble in an aqueous fermentation broth and for which the use of a solvent for extraction purposes is impossible or impractical. In such a case, the solid product of interest must be separated from both the solid cell mass phase and the liquid phase fermentation broth. Methods for such separations are not common. One possibility is to take advantage of any difference in particle size to filter the solids from one another. Another is to take advantage of differences in density and settle the solids at different rates, leading to separation. This invention shows that by actually solubilizing the cell mass, resulting in a liquid phase and solid (product-containing) phase, typical liquid-solid separation techniques can then be used to separate the solid product from the cell mass.

SUMMARY OF THE INVENTION

There is described a process for the recovery of desired insoluble fermentation products from a cell mass-containing fermentation broth, wherein one solid phase of the fermentation broth contains the desired product and the second solid phase of the fermentation broth contains the bio or cell mass. The recovery process comprises treating the fermentation broth comprising both solid phases to solubilize the cell mass portion only, while not adversely affecting the solubility of the desired product portion. This results in a solid phase and a liquid phase which subsequently can be separated by known liquid-solid separation techniques.

In an embodiment of the invention, the solubilization of the cell mass phase is affected by treating the fermentation broth with an appropriate acid or alkali at an elevated temperature to solubilize the cell mass, resulting in a solid-liquid phase which can more easily be separated to recover the desired product. In an aspect of this invention, the treatment with a acid or alkali may be a single step leading to the recovery of the desired product or the alkali/acid treatment step may optionally be repeated one or more times whereby after the original acid/alkali treatment step is carried out, resulting in a solid-liquid broth, the liquid may be discarded and the remaining solid phase (which is primarily the desired product but which also may contain cell mass or other debris) may be further treated with either an appropriate acid or alkali to further solubilize any residual, unsolubilized cell mass.

In another embodiment of this invention, the cell mass in the solid phase of the fermentation broth may be solubilized by enzymatic treatment of the cell mass. Specifically, the fermentation broth can be treated with one or more enzymes to break open the cells. The lysed cells are then separated from the product-containing phase by methods known to those skilled in the art. Such enzymatic treatment may optionally be followed by additional acid/alkali treatments as described above.

In a preferred embodiment of the present invention, the desired product is an insoluble product, for example, indigo, melanin, glucan or derivatives thereof.

DETAILED DESCRIPTION OF THE INVENTION

Figure 1:
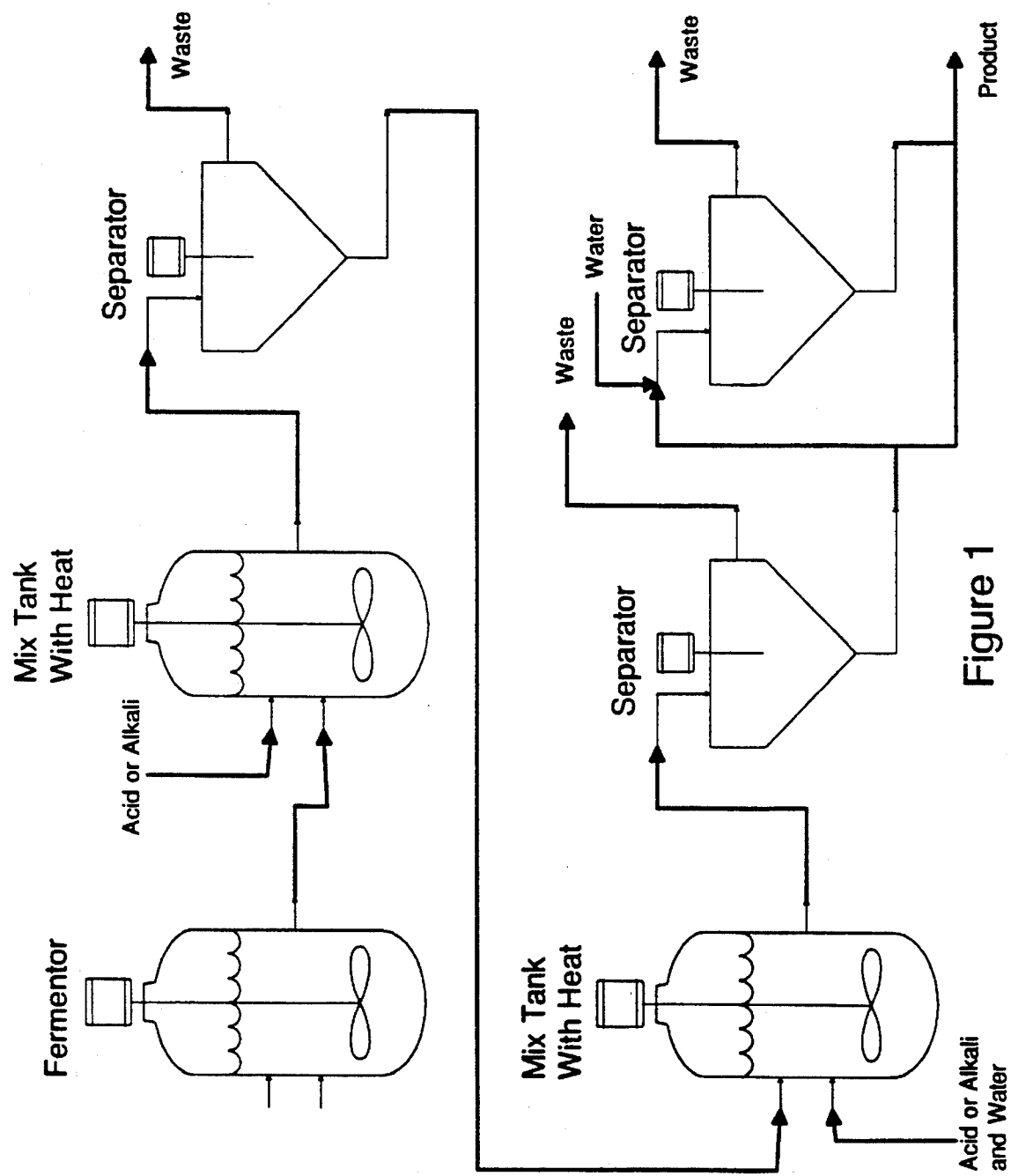
FIG. 1 is a generalized schematic of the recovery process of the present invention.

Most fermentation products are soluble in the fermentation broth and, thus, are easily recovered by standard methods. In the situation where a fermentation product is insoluble, special problems are faced when attempting to recover the insoluble product. For example, insoluble products may be recovered or purified by extraction into a solvent in which it is more soluble than the aqueous fermentation broth, thus, separating the product from the cell mass. The present invention shows that by solubilizing the cell mass rather than the product, typical liquid-solid separation technology can be used to separate the desired solid product from the cell mass.

Biosynthetic pathways can be specifically manipulated to enhance activity of enzyme complexes to increase productivity of chemical intermediates and to potentially alter end products of complex biologic systems in bacterial fermentative processes. Generally, by genetically manipulating biosynthetic pathways, it is now possible to produce commercial scale quantities of specialty and complex chemicals through bacterial fermentation as opposed to complex synthetic organic chemical reactions. This biosynthetic production of chemical compounds provides an economical and environmentally favorable alternative to chemical synthesis.

U.S. Pat. No. 4,520,103 (incorporated herein by reference) describes processes for the microbial production of indigo in genetically transformed microorganisms grown in an indole-free medium. U.S. Pat. No. 5,173,425 (incorporated herein by reference) describes a process for the enhancement of naphthalene dioxygenease activity in organisms that have been transformed with DNA encoding the expression of a multiple component naphthalene dioxygenase enzyme. These cells are capable of producing indigo when cultured in the presence of indole. It has been found that compounds such as indigo can now be produced from a starting material such as glucose in a de novo synthesis. Murdock, et al., *Bio Tech*, Vol. 11, p. 381–386. Other chemicals such as quinic acid and catechol have also been produced biosynthetically starting from glucose. (See, for example, U.S. Pat. No. 5,168,056, U.S. Ser. Nos. 07/906,976 and 07/389,738, the disclosure of which are incorporated herein by reference.) Other compounds such as melanin, a heterologous polymer of indole and carboxy-indole, may be made by biosynthetic process. (See, for example, EP 0 363 792 A1 and WO92/00373.)

As described above, the biosynthetic production of such chemical compounds is advantageous from an environmental and cost-effectiveness perspective. However, the recovery of such products from a fermentation broth medium may lead to unique problems if the resulting product is insoluble, such as indigo, melanin or glucan. The present invention provides a method for the high yield recovery of purified insoluble products from a fermentation broth.

As used herein, a "desired insoluble fermentation product" means any product made by means of a fermentation which is insoluble in the fermentation broth. Examples include but are not limited to indole-like compounds such as indigo, glucan, melanin and related polymer compounds. These compounds are listed as examples of insoluble fermentation products only and in no means are meant to limit the present invention. The techniques described herein can be applied to any insoluble fermentation product.

As used herein "cell mass" or "bio mass" means any cells or cell fragments, recombinant or natural, that can be propagated in liquid culture to produce solid products.

Common cells for the production of fermentation products include but are not limited to organisms from the genera Escherichia, Pseudomonas, Klebsiella, Schizophyllum, Chromobacterium, Streptomyces, Corynebacterium, Brevibacterium, Bacillus, Penicillium, Aspergillus, Trichoderma, Candida, Saccharomyces, Neurospora, and Acromonas. The cells, used to produce the desired compound, may be recombinant or naturally-occurring organisms which have been modified by standard methods known to those skilled in the art.

As used herein, an appropriate alkali means any compound which when used in sufficient quantities results in an increase of the pH of the fermentation broth to a point where the cell mass is solubilized. Such alkali compounds include but are not limited to potassium hydroxide, sodium hydroxide and ammonia.

As used herein, an appropriate acid means any compound which when used in sufficient quantities results in a reduction of the pH of the fermentation broth to a point where the cell mass is solubilized. Such acid compounds include but are not limited to sulfuric acid, hydrofluoric acid, hydrochloric acid, hydrobromic acid, hydroiodic acid, phosphoric acid, perchloric acid, nitric acid, formic acid and acetic acid. Preferred alkalis and acids are those used in the examples.

As used herein "elevated temperature" means any temperature over room temperature, preferably from about 40°–100° C., and most preferably from about 90°–95° C. It is understood that lower temperatures may work in the present process, however, it has been found that by increasing the temperature of the alkali or acid treatment, the rate of solubilization is increased thereby improving the efficiency and cost-effectiveness of the overall recovery process.

As used herein "an appropriate period of time" means a sufficient period of time to solubilize substantially all of the cell mass. It is understood that the time period necessary for such solubilization will vary depending on the amount of alkali or acid added, the temperature at which the reaction is carried out (higher temperature results in shortened time period) and other factors readily understood by those skilled in the art of recovery of fermentation products. The time period may be from about 1–12 hours.

It is contemplated that the recovery of an insoluble fermentation product could also be affected by contacting the fermentation broth with an appropriate enzyme to lyse the cell mass, thus, forming a separate phase capable of being separated from the solid (insoluble) product-containing phase. Suitable enzymes include but are not limited to lysozyme, protease, Dnase, Rnase, cellulase, protease, and amylase or any combination thereof. It is further contemplated that the gene encoding such enzyme could be inserted into the organism used to make the insoluble product, such gene being induced by appropriate regulatory controls only after the fermentation has been completed (during the recovery process). In such a process, no exogenous additions would be required to solubilize the cell mass as the enzymes required for lysis and solubilization would be produced by the cell mass.

Once the cell mass has been solubilized the liquid can be separated from the insoluble product by means of standard liquid-solid separation operations. These could include but are not limited to filtration, gravity sedimentation and centrifugation.

Filtration is defined in *Fermentation and Biochemical Engineering Handbook* (Ed. H. C. Vogel, Noyes Publications, 1983) as ". . . the process of separating solids from liquids by forcing the liquid through a filter media which may be a screen or woven textile, a bed of sand or diatomaceous earth, or a porous material like glass foam or sintered metal. The solids are retained on the media." Newer filter media include polymers and ceramics. The type of filter media and equipment used will depend upon the desired property of the final product. If the liquid is the product, clarity of the filtrate will be of primary concern. If the product is to be dried, removal of the maximum amount of liquid will be desired.

Gravity sedimentation is the separation of solid particles from a liquid by gravity settling. Such devices are typically characterized by an inlet designed to minimize turbulence, means for moving solids to a discharge point and means for removal of clarified liquid.

In centrifugation, centrifugal force is applied to replace or enhance the force of gravity to remove solid particles from a liquid. Any rotating machine used to impart a phase separation can be classified as a centrifuge.

In the present invention, unlike the more common liquid-solid separations described above, the desired product is in a solid phase, as is the cell mass phase. Thus, it is necessary to solubilize one or the other phase. We have found that by solubilizing the cell mass phase as described herein, the desired product (and the activity thereof) will not be adversely affected. This separation is generally affected as follows and as detailed in the experiments below.

As shown schematically in FIG. 1, the fermentation broth containing cell mass and the desired product is removed from the fermentor and placed in a tank where it is contacted with acid or alkali and heated. This will cause a substantial amount of the cell mass to be solubilized so it can be separated from the solid product by any of a number of solid-liquid separation methods. Substantial solubilization of the cell mass is, of course, dependent on the condition and amount/nature of acid or alkali added. Generally, one would desire at least about 20% solubilization of the cell mass on the first alkali/acid treatment. The level of solubilization is reflected in the increased degree of purity of the desired product with each sequential treatment. This process can be repeated one or more times (resolubilization) to further solubilize any residual cell mass in the remaining solid phase. Addition of water can be utilized to further wash the solid phase if needed. A washing step may be necessary to dilute out or wash away cellular debris from the desired product.

Once the desired product has been recovered by the process described herein, the product may optionally be further purified by methods known to those skilled in the art.

EXPERIMENTAL

Although the following examples relate to the recovery of indigo, the examples are not intended to limit the disclosure herein. Further aspects and advantages of the present invention will become apparent upon consideration of the following examples and preferred embodiments of the present invention.

Example 1: Strain for Indigo Production

Indigo is produced by a culture of recombinant *E. coli* harboring a plasmid encoding the genes for naphthalene dioxygenase from *Pseudomonas putida*. The strain used is FM5 transformed with plasmid Fd-911 described by Serdar, et al. (U.S. Pat. No. 5,173,425, the disclosure of which is incorporated herein by reference).

Example 2: Production of Indigo By Recombinant *Escherichia coli*

The organism from Example 1 can be grown in a 14-L fermentor under glucose-fed batch operation in a minimal salts medium. The temperature is controlled at 35° C., the pH at 7.0 and the dissolved oxygen at 20% of air saturation. L-tryptophan is fed to produce indigo. The L-tryptophan is first converted to indole by the action of the enzyme tryptophanase encoded on the chromosome of FM5. The indole is then converted to indigo by the action of the naphthalene dioxygenase enzyme system encoded by the plasmid-borne genes. Up to 20 g/L indigo can be produced by such a process.

Example 3: Recovery of Indigo with Two Alkali Treatments

Figure 2:
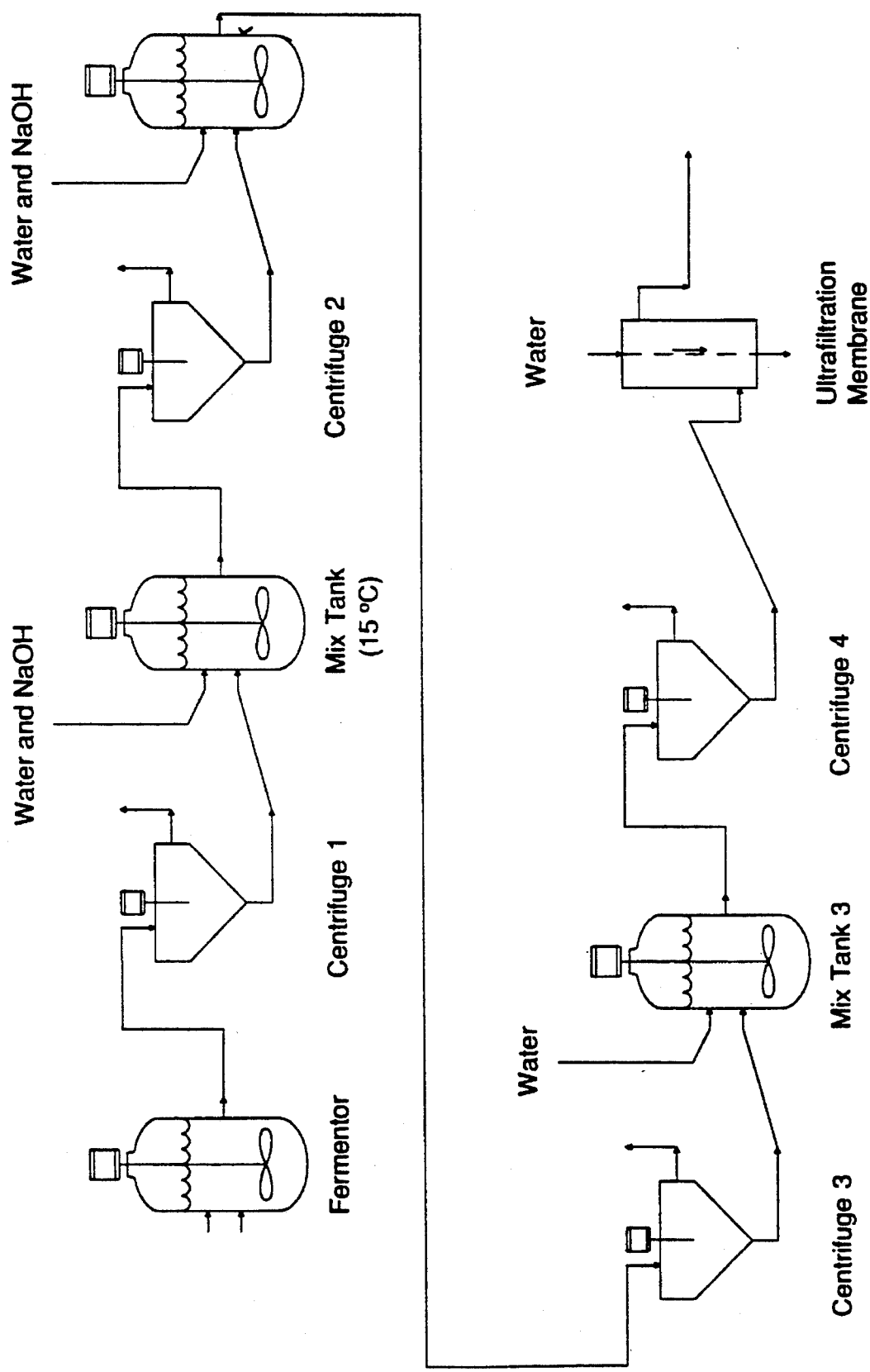
FIG. 2 is a schematic of the recovery process described in Example 3, wherein two alkali treatments are used to recover the insoluble product.

An indigo-containing fermentation broth with 12.0 g/L indigo and 147 g/L total solids (8.2% indigo purity) made such as described in Example 2, was recovered as shown in FIG. 2. Indigo purity after the various steps is summarized in Table 1. An initial centrifugation was attempted to specifically separate indigo from cell mass but no separation was observed. The material was resuspended in water to 14.0 g/L indigo and NaOH was added to a final concentration of 1%. This was held for 12 hours at 15° C. After being passed through a centrifuge, the resulting sludge contained 158 g/L indigo and 232 g/L total solids for an indigo purity of 68%, an increase of a factor of eight. Water and NaOH were added to give 115 g/L indigo and 5% NaOH and the mixture was heated to 90° C. and held for 12 hours. Centrifugation was followed by resuspension to the original volume with water and a second centrifugation. The resulting sludge had 366 g/L indigo and 401 g/L total solids for an indigo purity of 91%.

TABLE 1

|  | Fermentor | Centrifuge 2 Sludge | Centrifuge 4 Sludge |
|---|---|---|---|
| Indigo (g/L) | 12.0 | 158 | 366 |
| Total Solids (g/L) | 147 | 232 | 401 |
| Indigo Purity (%) | 8.2 | 68.1 | 91.3 |

Example 4: Recovery of Indigo with One Alkali and One Acid Treatment

Figure 3:
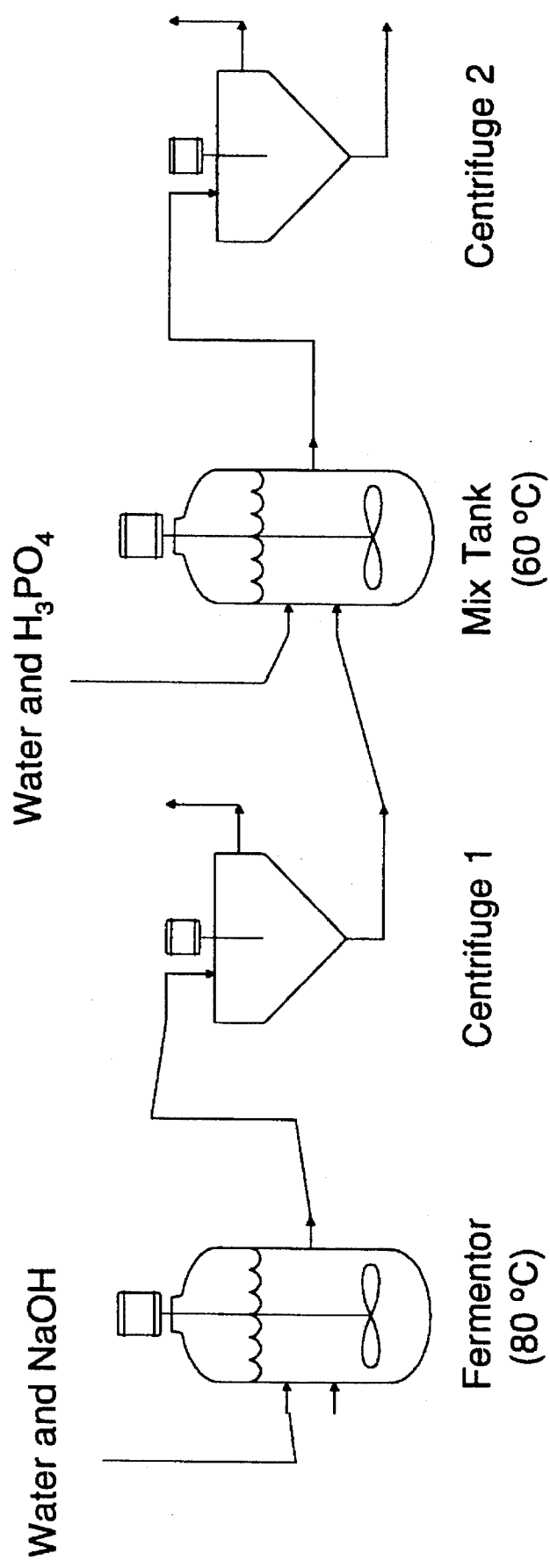
FIG. 3 is a schematic of the recovery process described in Example 4, wherein one alkali and one acid treatment is used to recover the insoluble product.

An indigo-containing fermentation broth with 12.0 g/L indigo and 237 g/L total solids (5.1% indigo purity) was recovered as shown in FIG. 3. Indigo purity after the various steps is summarized in Table 2. Water and NaOH, to a final concentration of 0.87%, were added directly to the fermentation broth and the mixture heated to 80° C. and held for 12 hours. The sludge from the resulting centrifugation contained 60.3 g/L indigo and 240 g/L total solids for an indigo purity of 25.1%. The sludge was resuspended in water and $H_3PO_4$ was added to a final concentration of 1.3%. This slurry was heated to 60° C. and held for 12 hours. After centrifugation, the sludge contained 97 g/L indigo and 122 g/L total solids for an indigo purity of 79.5%.

TABLE 2

|  | Fermentor | Centrifuge 1 Sludge | Centrifuge 2 Sludge |
|---|---|---|---|
| Indigo (g/L) | 12.0 | 60.3 | 97.0 |
| Total Solids (g/L) | 237 | 240 | 122 |
| Indigo Purity (%) | 5.1 | 25.1 | 79.5 |

Example 5: Recovery of Indigo with One Alkali Treatment

Figure 4:
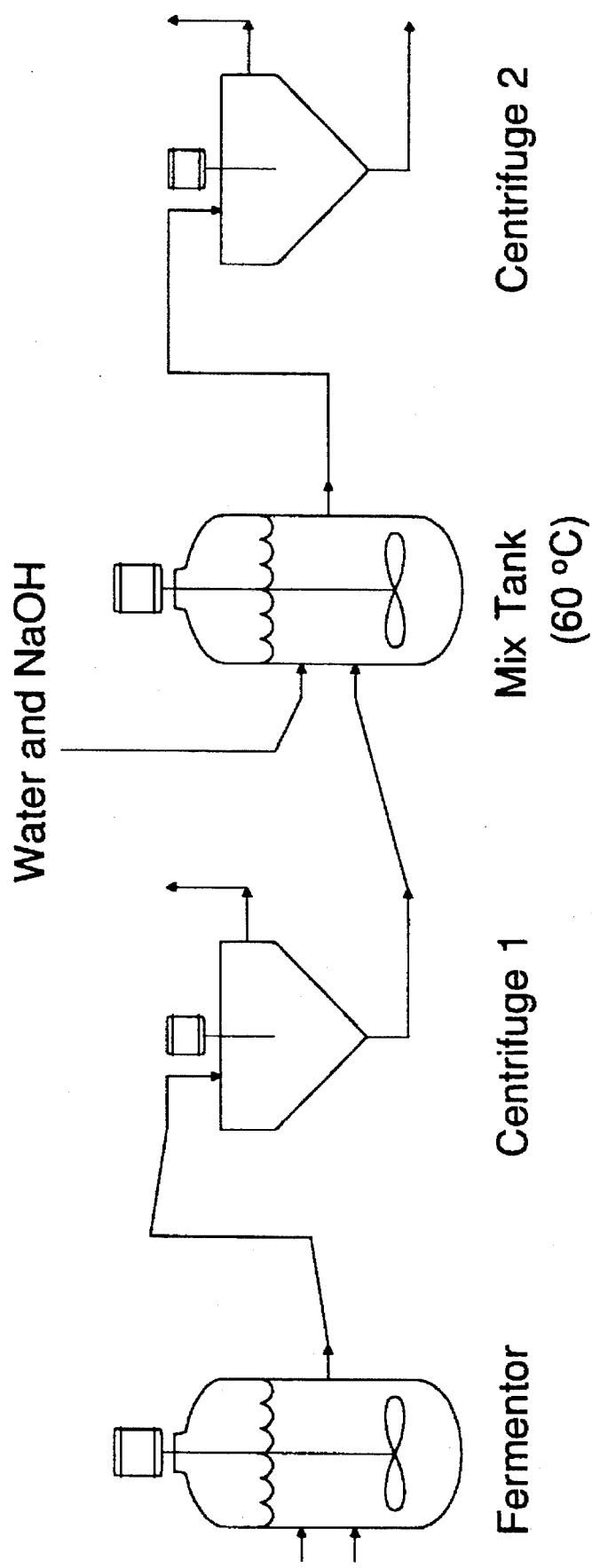
FIG. 4 is a schematic of the recovery process described in Example 5, wherein one alkali treatment is used to recover the insoluble product.

An indigo-containing fermentation broth was recovered as shown in FIG. 4. Indigo purity after the various steps is summarized in Table 3. The sludge from an initial centrifugation contained 23.5 g/L indigo and 182 g/L total solids for an indigo purity of 12.9%. Water was added and NaOH to a final concentration of 0.4%. The temperature was raised to 60° C. and held for 12 hours. After centrifugation, the resulting sludge contained 41.2 g/L indigo and 53.5 g/L total solids for an indigo purity of 77.0%.

TABLE 3

|  | Centrifuge 1 Sludge | Centrifuge 2 Sludge |
|---|---|---|
| Indigo (g/L) | 23.5 | 41.2 |
| Total Solids (g/L) | 182 | 53.5 |
| Indigo Purity (%) | 12.9 | 77.0 |

What is claimed is:

1. A process for recovering indigo from an aqueous fermentation broth comprising a first solid phase containing indigo and a second solid phase containing cell mass, the process consisting of:

a) contacting the fermentation broth with an alkali selected from the group consisting of potassium hydroxide, sodium hydroxide and ammonia at a temperature of from about 40° to 100° C. for a period of time sufficient to solubilize at least about 20% of cell mass;

b) separating the first solid phase containing indigo from the aqueous broth;

c) resuspending the first solid phase containing indigo with an alkali selected from the group consisting of potassium hydroxide, sodium hydroxide and ammonia, or an acid selected from the group consisting of phosphoric acid, sulfuric acid, hydrochloric acid, nitric acid and perchloric acid, or a combination of said alkali and said acid, at a temperature of from about 40° to 100° C. for an appropriate period of time to solubilize residual cell mass;

d) separating the first solid phase containing indigo from the aqueous broth; and e) recovering the indigo from the first solid phase.

2. A process of claim 1 wherein the alkali is sodium hydroxide and the acid is phosphoric acid.

3. A process of claim 1 wherein the temperature is from about 90°–95° C.

4. A process of claim 3 wherein each alkali and acid step is carried out for a period of from about 1 to 12 hours.

5. A process of claim 1 further comprising purifying the indigo product resulting from such recovery process.

* * * * *